(12) United States Patent
Ohga et al.

(10) Patent No.: US 10,294,509 B2
(45) Date of Patent: May 21, 2019

(54) METHOD FOR MEASURING ETHANOLAMINE PHOSPHATE

(71) Applicant: Human Metabolome Technologies, Inc., Tsuruoka-shi, Yamagata (JP)

(72) Inventors: Takushi Ohga, Tsuruoka (JP); Yoshiaki Ohashi, Tsuruoka (JP)

(73) Assignee: HUMAN METABOLOME TECHNOLOGIES, INC., Tsuruoka-shi, Yamagata (JP)

( * ) Notice: Subject to any disclaimer, the term of this patent is extended or adjusted under 35 U.S.C. 154(b) by 0 days.

(21) Appl. No.: 15/456,063

(22) Filed: Mar. 10, 2017

(65) Prior Publication Data

US 2017/0198334 A1    Jul. 13, 2017

Related U.S. Application Data

(62) Division of application No. 14/237,488, filed as application No. PCT/JP2012/078749 on Nov. 6, 2012, now Pat. No. 9,631,224.

(30) Foreign Application Priority Data

Nov. 10, 2011  (JP) ................. 2011-246881

(51) Int. Cl.
| | | |
|---|---|---|
| C12Q 1/52 | (2006.01) | |
| C12Q 1/32 | (2006.01) | |
| C12N 9/10 | (2006.01) | |
| C12N 9/88 | (2006.01) | |

(52) U.S. Cl.
CPC ............. *C12Q 1/52* (2013.01); *C12N 9/1096* (2013.01); *C12N 9/88* (2013.01); *C12Q 1/32* (2013.01)

(58) Field of Classification Search
CPC ....................................................... C12Q 1/32
See application file for complete search history.

(56) References Cited

U.S. PATENT DOCUMENTS

| | | | |
|---|---|---|---|
| 6,103,471 A | 8/2000 | Bandman et al. | |
| 2008/0229451 A1* | 9/2008 | Cao ...................... | C07K 14/195 800/281 |

FOREIGN PATENT DOCUMENTS

| | | |
|---|---|---|
| CN | 85105297 | 3/1987 |
| JP | 63-214199 | 9/1988 |
| JP | 02-207789 | 8/1990 |
| JP | 09-37796 | 2/1997 |
| JP | 2001-157579 | 6/2001 |
| JP | 2008-253258 | 10/2008 |
| WO | 2006/105907 | 10/2006 |
| WO | 2011/019072 | 2/2011 |

OTHER PUBLICATIONS

Fleshood et al: "The Metabolism of O-Phosphorylethanolamine in Animal Tissues"; The Journal of Biological Chemistry, vol. 245, No. 17, Issue of Sep. 10, pp. 4414-4420 (1970).
Fleshood et al: "O-Phosphorylethanolamine Ammonia Lyase, A New Pyridoxal Phosphate-Dependent Enzyme"; Biochemical and Biophysical Research Communications, vol. 36, No. 1, pp. 110-118 (1969).
Jones et al: "Microbial Metabolism of Amino Alcohols 1-Aminopropan-2-OL and Ethanolamine Metabolism via Propionaldehyde and Acetaldehyde in a Species of Pseudomonas"; Biochemical Journal, 134, pp. 167-182 (1973).
Bartsch, K. et al.: "L-2amino-4-methylphosphinobutyric acid-specific transaminase [synthetic construct]"; GenBank, CAA00691.1 (1993), 1 page.
Extended European Search Report, dated May 8, 2015; European Patent Application No. 12848737.8, 11 pages.
Sherif et al.: "Gamma-Aminobutyrate Aminotransferase Activitiy in Blood Platelets of Six Species"; Comparative Biochemistry and Physiology, vol. 104C, No. 2, Feb. 1993, pp. 345-349.
Toney et al.: "Active site model for γ-aminobutyrate aminotransferase explains substrate specificity and inhibitor reactivities"; Protein Science, vo. 4, No. 11, Nov. 1995, pp. 2366-2374.
Chinese Office Action, dated Jun. 17, 2015; Chinese Patent Application No. 201280039054.8, 7 pages.
Boubekeur et al., "Participation of acetaldehyde dehydrogenases in ethanol and pyruvate metabolism of the yeast *Saccaromyces cerevisiae*", Eur. J. Biochem., vol. 268, pp. 5067-5065, 2001.
Faulkner et al., "Microbial Metabolism of Amino Alcohols", Biochem. J., vol. 138, pp. 263-276, 1974.

* cited by examiner

*Primary Examiner* — Bin Shen
(74) *Attorney, Agent, or Firm* — Hamre, Schumann, Mueller & Larson, P.C.

(57) ABSTRACT

To provide a method for simply measuring ethanolamine phosphate in a sample, and a reagent, kit, program and the like useful in the method.
A measurement method of ethanolamine phosphate includes a first step of adding an enzyme, which can catalyze a reaction that forms acetaldehyde from ethanolamine phosphate, to a sample, and conducting a first enzymatic reaction to form acetaldehyde, phosphoric acid and ammonia; and a second step of quantifying at least one of the resultant acetaldehyde, phosphoric acid and ammonia to determine an amount of the ethanolamine phosphate in the measurement sample.

7 Claims, 6 Drawing Sheets
Specification includes a Sequence Listing.

[FIG. 1]
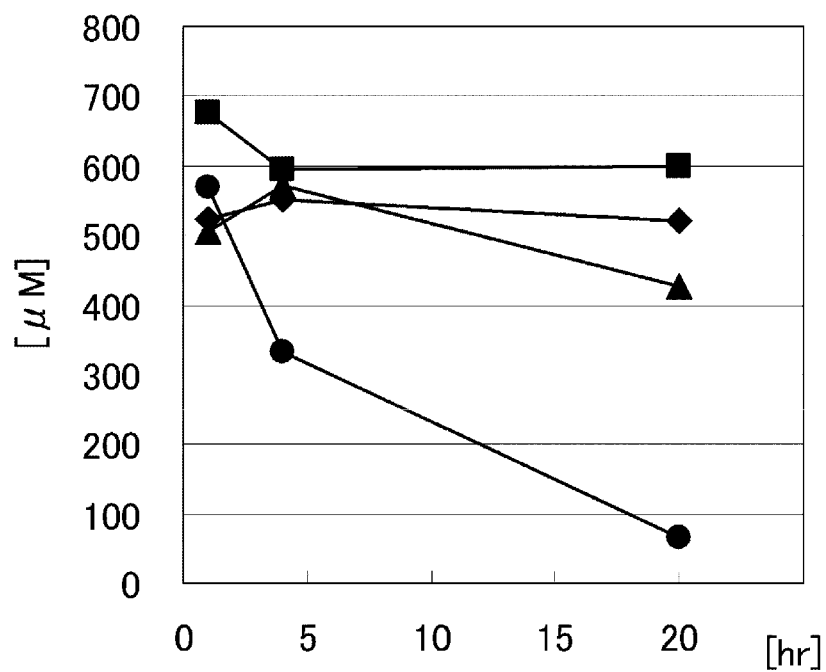

[FIG. 2]
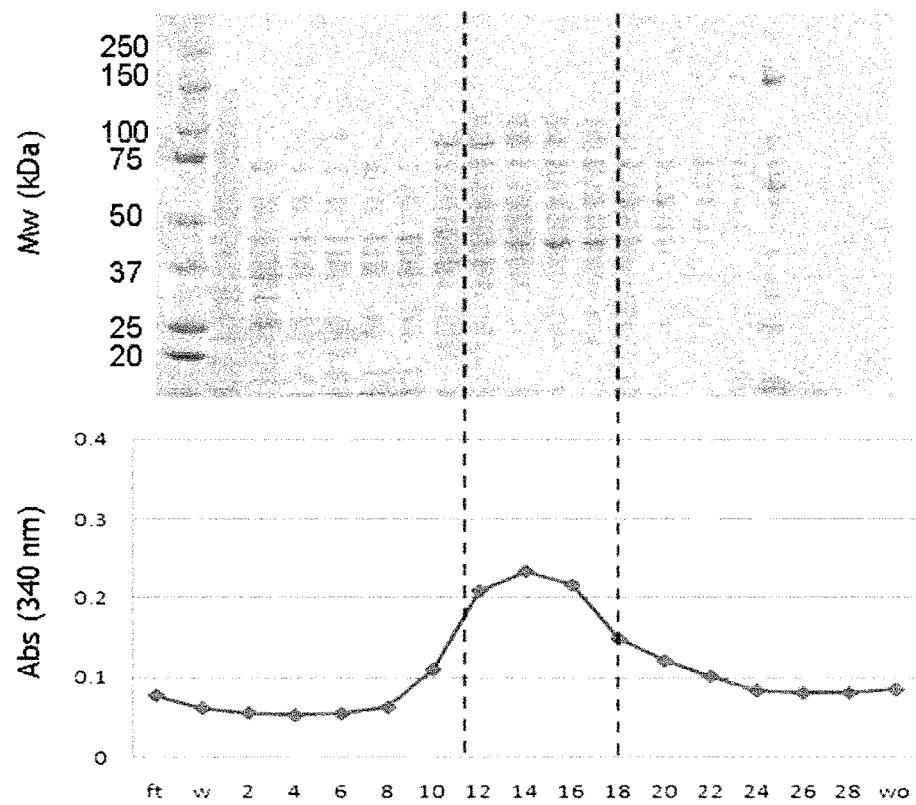

[FIG. 3]
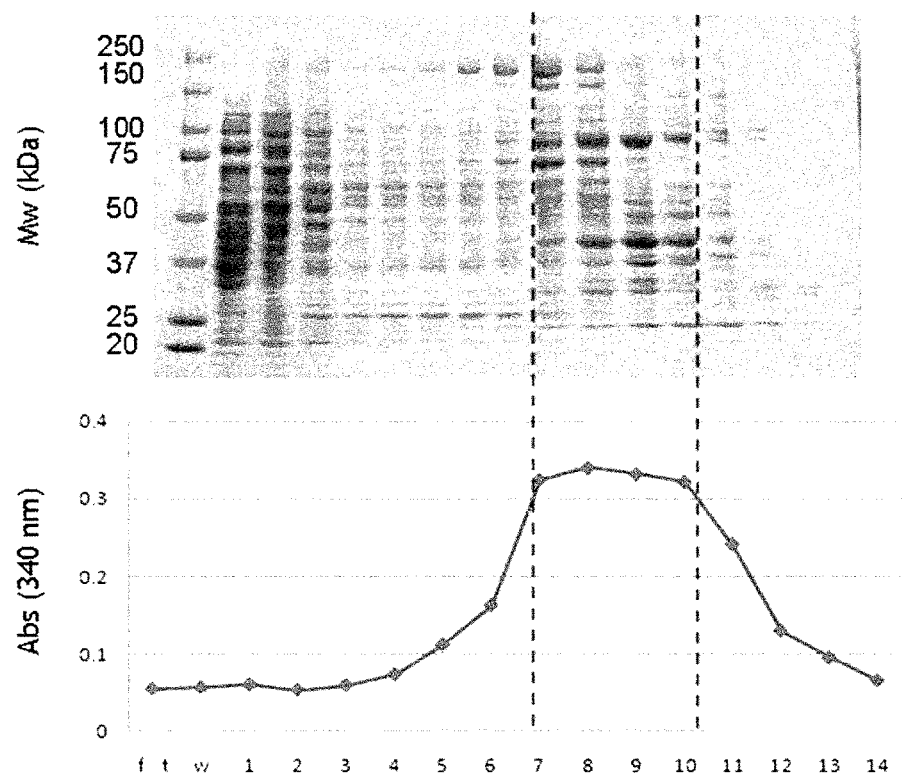

[FIG. 4]
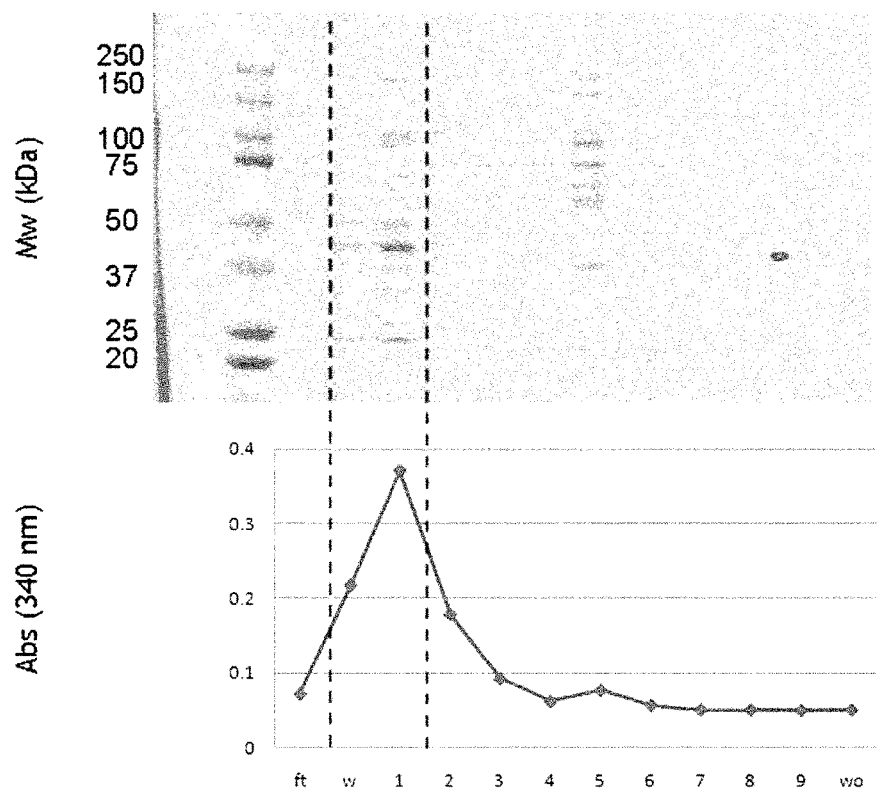

[FIG. 5]
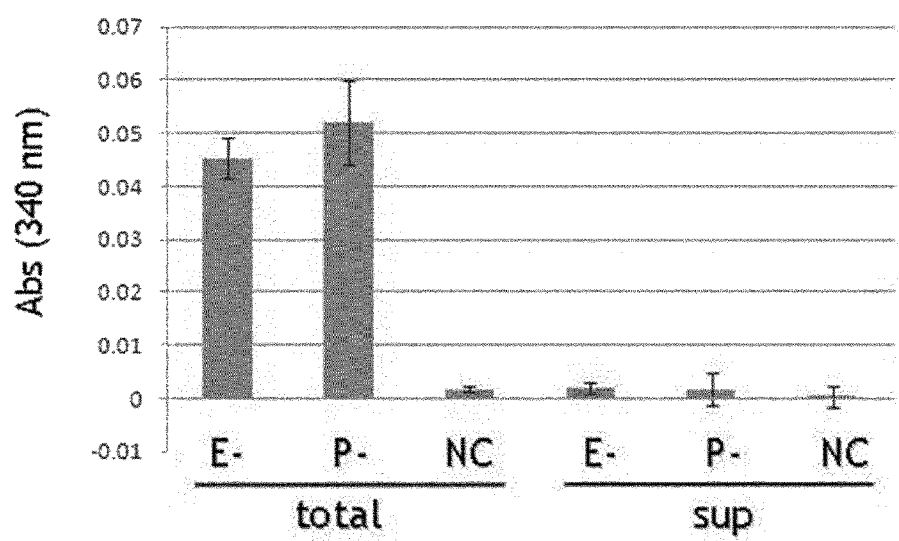

[FIG. 6]

```
                          20                    40                    60
                           |                     |                     |
SEQ ID NO: 1  GabT Panan  MQNVLAEQQT YADN------ ---------- ---------- ---------- ------SQLL DVRDHNVPRG 28
SEQ ID NO: 2  GabT Ecoi   MNS------- ---N------ ---------- ---------- ------KELM QRRSQAIPRG 18
SEQ ID NO: 4  GabT Stok   MLS-----RK IIEE------ ---------- ---------- ---------- ------SDIY LATSTRDP-- 21
SEQ ID NO: 5  GabT Hsap   MC-ELYS-KR DTLGL----- ---------- ---------- ---------- ----RKKHIGPS 21
SEQ ID NO: 6  GabT Mmus   MAADTRA-KA VTLDL----- ---------- ---------- ---------- ---RRRLLSSS 22
SEQ ID NO: 7  GabT Atha   MALQRQLLKR ATSDIYHRRA ISLLRTDFST SPSIADAPPH IPPFVHQPRP YKGPSADEVL QKRKKFLGPS 70
              Consensus   M******-K* *TL----- ---------- ---------- ---------- --R*****S 80                    100                   120                   140
                           |                     |                     |                     |
             GabT Panan   IITAH---PL VIERAKGSEV WDVEGNRYLD FVGGIGVLNV GH-NHPAVVN AVTRQLGMVS HACFQVAAYP 94
             GabT Ecoi   VGQIH---PI FADRAENCRV WDVEGREYLD FAGGIAVLNT GH-LHPKVVA AVEAQLKKLS HTCFQVLAYE 84
             GabT Stok   --ELF---PL VIDHGEGVWI YDVDGNKYLD FTSGIGVNNL GWPSHPEVIK IGIEQMQKLA HAAAANDFYNI 86
             GabT Hsap   CKVFFASDPI KIVRAQRQYM FDENGEQYLD CINNVAHV-- GH-CHPGVVK AALKQMELL- NTN-SRFLHD 86
             GabT Mmus   CRLFFPEDPV KIIRGQGQYL YDEQGREYLD CINNVAHV-- GH-CHPTVVQ AAHEQNLVL- NTN-SRYLHD 87
             GabT Atha   LFHYY-QKPL NIVEGKMQYL YDESGRRYLD AFAGIVTVSC GH-CHPDILN AITEQSKLLQ HAT-TIYLHH 137
              Consensus   ******.*DP* *I*R****** *DGYLD *GI*N* GH-*HP*VV* A*Q*L* HF****

160                   180                   200
                           |                     |                     |
             GabT Panan   GYIELAQRLN KLVGGDEHYK SVFFTSGAEA VENAVKIARS YTQRPGIIAF DGAFHGRTLL GVTLTGMSAP 164
             GabT Ecoi   PYLELCEIMN QKVPGDFAKK TLLVTTGSEA VENAVKIARA ATKRSGTIAF SGAYHGRTHY TLALTGKVNP 154
             GabT Stok   PQLELAKKLV TYSPGNFQKK VFFSNSGTEA IEASIKVVKN -TGRKYIIAF LGGFHGRTFG SISLTASKAV 155
             GabT Hsap   NIVEYAKRLS ATLPEKL-SV CYFTNSGSEA NDLALRLARQ FRGHQDVITL DHAYHGHLSS LIEISPYK-- 153
             GabT Mmus   NIVDYAQRLS ETLPEQL-SV FYFLNSGSEA NDLALRLARQ YTGHQDVVVL DHAYHGHLSS LIDISPYK-- 154
             GabT Atha   AIGDFAEALA KMPGNL-KV VYFVNSGSEA NELAMMMARL YTGSLEMISL RNAYHGGSSN TIGLTALN-- 204
              Consensus   ***E*A**L* *PG* F*NSGSEA *E*A***AR* YTG**I AYHG** *I*LT****AP 220                   240                   260                   280
                           |                     |                     |                     |
             GabT Panan   YKQNFGPFPG DVYRLPFPNP ------LHGV TEADCLKAL- -----DQLFS VQILPERVAA IIIEPVQGDG 222
             GabT Ecoi   YSAGMGLMPG HVYRALYPCP ------LHGI SEDDAIASI- -----HRIFK NDAAPEDIAA IVIEPVQGEG 212
             GabT Stok   QRSIVGPFMP GVIHVPYPNP YRNPWHINGY ENPSELVNRV IEFIEDYIFV NLVPPEEVAG IFFEPIQGEG 225
             GabT Hsap   FQKGKDVKKE FVHVAPTPDT YRGKYR---- EDHADSASAY ADEVKKIIED AHNSGRKIAA FIAESMQSCG 219
             GabT Mmus   F-RNLGGQKE WVHVAPLPDT YRGPYR---- EDHPNPAEAY ANEVKHVISS AQQKGRKIAA FFAESLPSVS 219
             GabT Atha   TWKYPLPQGE IHHVV-NPDP YRGVFG---- SD----GSLY AKDVHDHIE- -YGTSGKVAG FIAETIQGVG 263
              Consensus   ***G** *V***P*P*P YRG***LHG* *******Y AV*I ******AA *E**QG*G 300                   320                   340
                           |                     |                     |
             GabT Panan   GFLPAGPAFM QALRRITTQH ┌GIMLICDEIQ SGFGRTG┐--- -MFAFQQLGI KPDMITTAKS LAGGL-PISG 288
             GabT Ecoi   GFYASSPAFM QRLRALCDEH │GIMLIADEVQ SGAGRTG│--- -LFAMEQMGV APDLTTFAKS IAGGF-PLAG 278
             GabT Stok   GYVIPPKNFF AELQKLAKKY │GILLVDDEVQ MGLGRTG│K-- -LFAIENFNT VPDVITLAKA LGGGIMPIGA 292
             GabT Hsap   GQIIPPAGYF QKVAEYVHGA │GGVFIADEVQ VGFGRVG│KHF WSFQMYGEDF VPDIVTMGKP MGNGH-PVAC 288
             GabT Mmus   GQIIPPAGYF SQVAEHIHRA │GGLFVADEIQ VGFGRIG│KHF WAFQLEGEDF VPDIVTMGKS IGNGH-PVAC 288
             GabT Atha   GAVELAPGYL KSVYEIVRNA │GGVCIADEVQ TGFGRTG│SHY WGFQT--QDV VPDIVTMAKG IGNGL-PLGA 330
              Consensus   G******* ****** │G*IADEVQ *GFGRTG│HF W*FE VPDT*AK* *G*G*.P***

360                   380                   400                   420
                           |                     |                     |                     |
             GabT Panan   VVGKAEIMDS PAPGGLG--G TYGGNALACA AALAVLDIFE QENLLARSCQ LGEQLNQRLR QLADKYACIG 356
             GabT Ecoi   VTGRAEVMDA VAPGGLG--G TYAGNPIACV AALEVLKVFE QENLLQKAND LGQKLKDGLL AIAEKHPEIG 346
             GabT Stok   TIFRKDL--D FKPGMHS--N TFGGNALACA IGSKVIDIVK --DLLPHVNE IGKIFAEELQ GLAD------ 328
             GabT Hsap   VVTTKEIAEA FSSSGMEYFN TYGGNPVSCA VGLAVLDIIE NEDLQGNAKR VGNYLTELLK KQKAKHTLIG 358
             GabT Mmus   MATTQAVSRA FEATGVEYFN TFGGNPVSCA VGLAVLDVLK TGKLQAHATN VGSFLLEHLT QQKAKHPIIG 358
             GabT Atha   VVTTPEIASV LASKIL--FN TFGGNPVCSA GGLAVLNVID KEKRQEHCAE VGSHLIQRLK DVQKRHDIIG 398
              Consensus   V**E G-FN T*GGNP**CA *GLAVLD*** *E*L****** *GL*L* **KHIG 440                   460                   480
                           |                     |                     |
             GabT Panan   DVRGVGFMQA VEIL-DVDTH KPDSALTQKI LDSACQEGLL LIKCGLHRNT IRFLAPLVTT DSQLEEALHI 425
             GabT Ecoi   DVRGLGAMIA IELFEDGDHN KPDAKLTAEI VARARDKGLI LLSCGPYYNV LRILVPLTIE DAQIRQGLEI 416
             GabT Stok   DVRGIGLAWG LEY------- -NEKKVRDRI IGESFKRGLL LLPAG--RSA IRVIPPLVIS EEEAKQGLDI 410
             GabT Hsap   DIRGIGLFIG IDLVKDHLKR TPATAEAQHI IYKMKEKRVL LSADGPHRNV LKIKPPMCFT EEDAKFMVDQ 428
             GabT Mmus   DVRGIGLFIG VDLIKDETLR TPATEEAEYL VSRLKENYIL LSIDGPGKNI LKFKPPMCFN VDNAQHVVAK 428
             GabT Atha   DVRGRGLMVG IELVSDRKDK TPAKAETSVL FEQLRELGIL VGKGGLHGNV FRIKPPMCFT KDDADFLVDA 468
              Consensus   DVRG*GL**G *ELD TP***I *****G*L L***GPH*N* *RPP *A******

500                   520                   540                   560
                           |                     |                     |                     |
             GabT Panan   FDIALARATG ---------- ---------- ---------- ---------- ----------R 436
             GabT Ecoi   ISQCFDEAK- ---------- ---------- ---------- ---------- ---------- 425
             GabT Stok   LKKVIKVVK- ---------- ---------- ---------- ---------- ---------- 419
             GabT Hsap   LDRILTVLEE AMGTKTESVT SENTPCKTKM LKEAHIELLR DSTTDSKENP SRKRNGMCTD TH--SLLSKR 496
             GabT Mmus   LDDILTDMEE ----KVRS-- ------CETLR IK-------- -------HP PE-------D THPTQILLTR 464
             GabT Atha   LDYSISRL-- ---------- ---------- ---------- ---------- ---------- 476
              Consensus   LD******E ---------- ---------- ---------- ---------- ---------R GabT Panan   LG* 439
             GabT Ecoi   --Q 426
             GabT Stok   --- 419
             GabT Hsap   LKT 499
             GabT Mmus   QQD 467
             GabT Atha   --- 476
              Consensus   L**
```

METHOD FOR MEASURING ETHANOLAMINE PHOSPHATE

CROSS-REFERENCE TO RELATED APPLICATION

This application is a Division of application Ser. No. 14/237,488 issues as U.S. Pat. No. 9,631,224, filed Feb. 6, 2014, which is a National Stage Application of PCT/JP2012/078749, filed Nov. 6, 2012, which claims foreign priority from Japanese Patent Application Number 2011-246881, filed Nov. 10, 2011.

TECHNICAL FIELD

This relates to a measurement method of the ethanolamine phosphate level in a sample.

BACKGROUND ART

Depression is a kind of mood disorder, and is accompanied by "depressed mood" and "loss of interest or pleasure" as primary symptoms. According to a survey among medical institutions in Japan, more than 700,000 depressive patients were considered to exist in 2008. However, a diagnosis of depression depends in a large part on the subjective view of a physician or psychologist about emotional aspects of a patient or on the subjective view and response of the patient himself or herself, and is hardly considered to be made through an objective determination. Attempts have, therefore, been made in recent years to identify a component in a body fluid of a patient as an objective guideline for the diagnosis of depression.

It has been reported to be able to determine, as a predictive marker for depression, the level of triptophan or its degradation product, the expression level of a specific gene, or the like in a body fluid (Patent Documents 1 and 2). In the meantime, the present inventors found that the ethanolamine phosphate level in blood is useful as a biomarker for diagnosing depression (Patent Document 3).

PRIOR ART DOCUMENTS

Patent Documents

Patent Document 1: WO-A-2006/105907
Patent Document 2: JP-A-2008-253258
Patent Document 3: WO-A-2011/019072

DISCLOSURE OF THE INVENTION

Problem to be Solved by the Invention

An ethanolamine phosphate level is highly reliable and excellent as a biomarker for depression, but its measurement has been limited to a measurement method that uses a CE-TOFMS (capillary electrophoresis time-of-flight mass spectrometry) system. However, measurements by CE-TOFMS are time consuming (30 to 40 minutes). Moreover, CE-TOFMS systems are expensive and precision analysis equipment. Because of this, CE-TOFMS systems are equipped in only a limited number of universities and analysis institutes. There is, accordingly, an outstanding need for establishing a quick and simple measurement method, which allows even local hospitals and clinics to measure an ethanolamine phosphate level as a biomarker for depression.

Objects of the present invention are, therefore, to provide a method for simply measuring the ethanolamine phosphate level in a sample, and also, a reagent, kit, program and the like useful in the method.

Means for Solving the Problem

The above-described objects can be achieved by the present invention to be described hereinafter. Described specifically, the present invention provides a measurement method of ethanolamine phosphate, comprising a first step of adding an enzyme, which can catalyze a reaction that forms acetaldehyde from ethanolamine phosphate, to a sample, and conducting a first enzymatic reaction to form acetaldehyde, phosphoric acid and ammonia; and a second step of quantifying at least one of the resultant acetaldehyde, phosphoric acid and ammonia to determine an amount of the ethanolamine phosphate in the measurement sample.

The enzyme may preferably be an enzyme having a GabT domain.

Advantageous Effects of the Invention

According to the present invention, there are provided a method for simply measuring the ethanolamine phosphate level in a sample and a reagent useful in the method, and a diagnostic agent capable of simply diagnosing depression.

BRIEF DESCRIPTION OF THE DRAWINGS

FIG. 1 is a graph showing ethanolamine phosphate (EAP)-degrading activity of a Pan lysate.

FIG. 2 illustrates a graph showing analysis results of another Pan lysate by anion chromatography (lower) and a graph showing SDS-PAGE results of respective factions (upper).

FIG. 3 illustrates a graph showing analysis results of some fractions of the another Pan lysate by hydrophobic chromatography (lower) and a graph showing SDS-PAGE results of respective sub-factions (upper).

FIG. 4 illustrates a graph showing analysis results of some other fractions of the another Pan lysate through a hydroxyapatite column (lower) and a graph showing SDS-PAGE results of respective sub-factions (upper).

FIG. 5 is a graph showing measurement results of ethanolamine phosphate-degrading enzyme activity in GabT expression systems.

FIG. 6 is a diagram showing alignment results of GabTs of SEQ ID NOS: 1, 2, 4, 5, 6, and 7.

MODES FOR CARRYING OUT THE INVENTION

In the method of the present invention for the measurement of an ethanolamine phosphate level, an enzyme which may hereinafter be called "the first enzyme" is used in the first step. The first enzyme catalyzes a reaction, which hydrolyzes ethanolamine phosphate (CAS Registry Number: 1071-23-4) to form acetaldehyde, phosphoric acid and ammonia and which is represented by the below-described reaction equation (1). This reaction may hereinafter be called "the first enzymatic reaction".

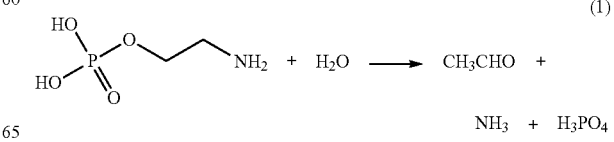

(1)

Heretofore, no enzyme has been identified yet to catalyze the one-step reaction of equation (1). However, the present inventors isolated an enzyme having catalyst activity for the above-described reaction from a *Pantoea ananatis* strain, and identified that enzyme to be γ-aminobutyrate aminotransferase (GabT).

In the measurement method of the present invention, at least one of acetaldehyde, phosphoric acid and ammonia formed through the enzymatic reaction is quantified in the second step to determine the amount of ethanolamine phosphate in the sample. Only one of acetaldehyde, phosphoric acid and ammonia may be subjected to the quantification, but the quantification of two or more of them makes it possible to reduce a measurement error.

When quantifying acetaldehyde in the second step, it can be quantified with good sensitivity by making use of the property of reduced nicotinamide adenine dinucleotide (NADH) that it absorbs 340 nm wavelength ultraviolet rays well. Specifically, a method comprising the following two sub-steps can be mentioned.

As the first sub-step, acetaldehyde dehydrogenase (ALDH) and oxidized nicotinamide dehydrogenase (NAD$^+$) are added to the measurement sample after the above-described first step to oxidize acetaldehyde in the sample to acetic acid [see equation (2)].

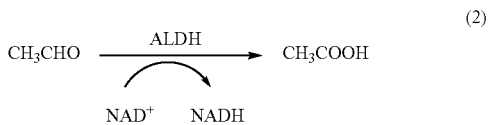

(2)

In this reaction, NAD$^+$ is reduced to NADH. Because only NADH strongly absorbs 340 nm ultraviolet rays, the measurement of the absorbance at 340 nm of the measurement sample after the reaction as the next sub-step can lead to quantifying the amount of acetaldehyde formed in the measurement sample after the first step, and from the value so quantified, the amount of ethanolamine phosphate in the measurement sample can be determined. Upon measurement of the acetaldehyde level in the second step, a commercial acetaldehyde quantification kit (for example, "F-Kit Acetaldehyde", product of Roche Diagnostics GmbH) can be used.

In the first step, it is preferred to use a coenzyme in combination so that the efficiency of the enzymatic reaction can be increased further. As a preferred coenzyme, pyridoxal phosphate can be mentioned.

No particular limitation is imposed on the enzyme for use in the first step insofar as it can catalyze the reaction of equation (1) that hydrolyzes ethanolamine phosphate to form acetaldehyde, phosphoric acid and ammonia in one step. As examples of the enzyme having this enzyme activity, enzymes having a GabT domain can be mentioned. The term "GabT domain" means an amino acid sequence region defined by GXXXBADEBQXGFZRXG, wherein X means an amino acid, B denotes a branched amino acid selected from the group consisting of I, L and V, and Z signifies G or A.

As will be made apparent in examples to be described subsequently herein, the present inventors found that in a wide variety of organism species including archaebacteria, prokaryotes and eukaryotes such as plants and animals, their amino acid sequences have high homology of at least 90% with the GabT domain of γ-aminobutyrate aminotransferase. As examples of the enzyme which has enzyme activity capable of catalyzing the reaction of equation (1) and can be suitably used in the first step, proteins with amino acid sequences having at least 90% of homology with the GabT domain can be mentioned.

Specific examples of the enzyme, which has enzyme activity capable of catalyzing the reaction of equation (1) and has a GabT domain, include a protein (SEQ ID NO: 1 in the accompanying sequence listing) having a GabT domain derived from *Pantoea ananatis* and a protein (SEQ ID NO: 2) having a GabT domain derived from *E. coli*, both of which were identified by the present inventors. For use in the first step of the measurement method according to the present invention, the enzyme can be any protein insofar as it has activity to catalyze the reaction of equation (1). Therefore, the enzyme may also be a protein consisting of an amino acid sequence similar to the amino acid sequence represented by SEQ ID NO: 1 or 2 except that one or a few amino acids have been deleted, substituted or added, or a protein consisting of an amino acid sequence having at least 90% of homology with the amino acid sequence represented by SEQ ID NO: 1 or 2. The enzyme may be in an unpurified form, and even a partial purification product or a cell lysate containing the enzyme is usable insofar as it has the enzyme activity. As an example of the cell lysate, a supernatant obtained by the centrifugation of a *Pantoea ananatis* lysate can be mentioned.

The method of the present invention for the measurement of an ethanolamine phosphate level is very simple in procedure, and can be incorporated as a system in existing clinical chemistry equipment. Described specifically, a measurement sample is set on a measurement system. After the first enzyme is added to the measurement sample and acetaldehyde, phosphoric acid and ammonia are formed, at least one of the acetaldehyde, phosphoric acid and ammonia is quantified. As this method involves no reliance on human subjective view, it is suited for routine processing by the measurement system and can lead to quickly and simply measuring a large number of samples. Such processing can also be performed by making a computer, which is incorporated in the measurement system, read a program that allows the measurement system to conduct the first step of adding the enzyme to each measurement sample and the second step of quantifying at least one of acetaldehyde, phosphoric acid and ammonia.

As described above, there is a significant correlation between the concentration of ethanolamine phosphate in plasma and depression (see Patent Document 3). By further adding, to the above-described program, a step of determining, based on the measurement value of ethanolamine phosphate level in a measurement sample, whether or not the subject who provided the measurement sample is a depressive patient and another step of outputting the measurement result so obtained, it is hence possible to diagnose whether or not the subject who provided the measurement sample is a depressive patient.

The program maybe recorded on a recording medium readable by a computer, or on a recording medium in a computer attached to the measurement system. The recording medium may be, but is not limited specifically to, a hard disk, CD, DVD, USB memory, Floppy® disk, or the like.

According to the present invention, there is also provided an ethanolamine phosphate-measuring reagent which contains an enzyme capable of catalyzing a reaction that forms acetaldehyde from ethanolamine phosphate. As the enzyme capable of catalyzing the reaction that forms acetaldehyde from ethanolamine phosphate, it is possible to use an enzyme similar to that employed in the first step of the measurement method of the ethanolamine phosphate level. Described specifically, proteins consisting of the amino acid sequences described under SEQ ID NO: 1 and SEQ ID NO: 2 in the sequence listing can be mentioned.

Preferably, the ethanolamine phosphate-measuring reagent may further contain a coenzyme for the enzyme to further improve the react ion efficiency of the enzyme. As a specific example of the coenzyme, pyridoxal phosphate can be mentioned. No particular limitation is imposed on the enzyme insofar as it can catalyze the reaction of the equation (1) that hydrolyzes ethanolamine phosphate to form acetaldehyde, phosphoric acid and ammonia in one step. As an example of the enzyme that has the enzyme activity, an enzyme having a GabT domain can be mentioned. As an alternative, the enzyme may be a protein having an amino acid sequence region having at least 90% of homology with the above-described GabT domain.

Since there is a significant correlation between the concentration of ethanolamine phosphate in plasma and depression as described above, the ethanolamine phosphate-measuring reagent can be used as a depression diagnostic agent.

According to the present invention, there is also provided an ethanolamine phosphate-measuring kit comprising a container with an enzyme, which can catalyze a reaction that forms acetaldehyde from ethanolamine phosphate, separately contained therein. Because the suffering from depression can be determined from the concentration of ethanolamine phosphate in plasma as described above, the use of the ethanolamine phosphate-measuring kit according to the present invention makes it possible to conduct screening of depressive patients from those subjected to an examination or check-up under a physical examination program or employees' in-house medical check-up program, to allow a non-specialist physician to conduct a diagnosis of a patient with suspected depression, or to allow a specialist to conduct a diagnosis along with an interview, to assess the effectiveness of treatment and to determine a strategy of treatment.

Preferably, the ethanolamine phosphate-measuring kit may further comprise another container with a coenzyme for the enzyme, said coenzyme being contained separately in said another container. As an example of the coenzyme, pyridoxal phosphate can be mentioned. No particular limitation is imposed on the above-described enzyme insofar as it can catalyze the reaction of equation (1) that forms acetaldehyde, phosphoric acid and ammonia in one step. As an example of the enzyme having the enzyme activity, an enzyme having a GabT domain can be mentioned. As an alternative, the enzyme maybe a protein having an amino acid sequence region having at least 90% of homology with the above-described GabT domain.

EXAMPLES

1. Preparation of Cell Lysate with Ethanolamine Phosphate-degrading Enzyme Contained Therein As cell strains having ethanolamine phosphate lyase activity, three Erwinia strains (Erwinia carotovora, *Pantoea ananatis* LMG 20103 strain, and *Erwinia milletiae*) were selected, and were purchased from Incorporated Administrative Agency, National Institute of Agrobiological Sciences. The three strains were subjected to liquid culture in portions of an oligotrophic synthetic medium with ethanolamine contained as a single nitrogen source therein. Resulting colonies were spread on LB plates and cultured overnight at 30° C., and colonies were obtained on the respective plates.

From each plate, two to three colonies were harvested, suspended in a liquid medium (2 to 5 mL), and cultured at 30° C. and 170 rpm. As pronounced proliferation was observed only on *Pantoea ananatis* out of the above-described three strains, that cell strain was cultured until $OD_{600}=1.0$, and subsequent to the culture, centrifugation was conducted to harvest its cells.

The thus-obtained cell strain was suspended in Buffer A [a solution of 2-mercaptoethanol (final concentration: 1 mM) in tris-hydrochloric acid buffer (final concentration: 50 mM), pH 7.5], cell disruption was conducted by sonication, and subsequent to centrifugation, a supernatant was collected to prepare a lysate (hereinafter called "the Pan lysate").

2. Measurement of Ethanolamine Phosphate-degrading Enzyme Activity of Pan Lysate Referential Example 1

To a reaction solution (1 mL) containing ethanolamine phosphate (final concentration: 2 mM) as a reaction substrate and pyridoxal phosphate (final concentration: 2 mM) as a coenzyme, the Pan lysate was added (final volume ratio: 5%), and the resulting mixture was incubated at 30° C. One hour later, the mixture (200 μL) was deproteinized by filtration ("MICROCON® (a centrifugal filter), Mw: 5k) to terminate the reaction. Subsequently, the concentration of ethanolamine phosphate in the filtrate was measured using a quadropole LC/MS mass spectrometer ("Quadropole LC/MS 6140" manufactured by Agilent Technologies, Inc.). A similar measurement was conducted on the sample after 4 hours and 20 hours from the initiation of the experiment. Results are indicated by black dots (●) in FIG. 1.

Referential Example 2

Measurements were conducted as in Referential Example 1 except for the use of a 10-fold dilute solution of the Pan lysate in Buffer A in place of the Pan lysate. Results are indicated by black triangles (▲) in FIG. 1.

Referential Example 3

Measurements were conducted as in Referential Example 1 except for the use of a 100-fold dilute solution of the Pan lysate in Buffer A in place of the Pan lysate. Results are indicated by black rhombi (◆) in FIG. 1.

Referential Example 4

Measurements were conducted as in Referential Example 1 except for the use of Buffer A, as a negative control, in place of the Pan lysate. Results are indicated by black squares (■) in FIG. 1.

From the results shown in FIG. 1, it is evident that the ethanolamine phosphate in each measurement sample was degraded and decreased in concentration with time by the enzyme in the Pan lysate. It was, therefore, demonstrated that an ethanolamine phosphate-degrading enzyme was contained in the Pan lysate.

3. Isolation of Ethanolamine Phosphate Lyase Derived from *Pantoea ananatis*

With the same culture medium and under the same conditions as in Item 1 described above, *Pantoea ananatis* was subjected to mass culture on the liquid medium. The thus-obtained cells were suspended in Buffer B [a solution of magnesium chloride (final concentration: 10 mM) in tris-hydrochloric acid buffer (final concentration: 20 mM), pH 7.5], cell disruption was conducted by sonication, and then, centrifugation was performed to obtain a supernatant fraction. The fraction was first subjected to elution fractionation under a gradient of sodium chloride (100-500 mM) by anion chromatography ("DE-52", product of GE Healthcare Japan Corporation), and then, SDS-PAGE was conducted on respective fractions. The respective fractions were added to portions of a tris-hydrochloric acid buffer (final concentration: 20 mM; pH 7.5), which contained ethanolamine phosphate (final concentration: 1 mM) and pyridoxal phosphate (final concentration: 1 mM), such that the final volume ratios of the fractions reached 30%. After the resulting mixtures were separately subjected to the reaction at 30° C., acetaldehyde dehydrogenase (ALDH) and oxidized nicotinamide dehydrogenase (NAD$^+$) were added to the respective samples after the reaction according to the manual of a commercial acetaldehyde quantification kit ("F-kit Acetaldehyde", product of Roche Diagnostics K.K.). Subsequent to the reaction of equation (2), the absorbances at 340 nm were measured. From each absorbance, the acetaldehyde in the corresponding sample after the reaction of equation (1) was quantified to determine the ethanolamine phosphate-degrading enzyme activity in the sample before the reaction of equation (1). The results of SDS-PAGE and the measurement results of ethanolamine phosphate-degrading enzyme activity are shown in an upper part and lower part of FIG. 2, respectively, such that each fraction in the upper graph and its corresponding fraction in the lower graph are aligned in the same column. The numbers in the lowest row are collected fraction numbers. "ft" means a flow-through, "w" denotes a wash solution (Buffer C-1) containing sodium chloride at 100 mM in Buffer B, and "wo" signifies awash solution (Buffer C-2) containing sodium chloride at 500 mM in Buffer. As shown in FIG. 2, strong ethanolamine phosphate-degrading enzyme activity was confirmed on the collected fractions numbered from 12 to 18. Further, it was considered from the results of SDS-PAGE that the bands around 75 kDa, 45 kDa and 40 kDa were likely those of ethanolamine phosphate-degrading enzymes.

The fractions numbered from 12 to 18 were then combined together, and the resulting solution was subjected to elution fractionation under ammonium sulfate (1-0 M) by hydrophobic chromatography ("Ether-650", product of Tosoh Corporation). As eluents, Buffer B and a solution (Buffer D-1) containing ammonium sulfate at 1 M in Buffer B were used. Similar to the above-described anion chromatography, SDS-PAGE and absorbance measurements using the acetaldehyde quantification kit were conducted on the respective fractions. Results are shown in FIG. 3. As shown in FIG. 3, high ethanolamine phosphate-degrading enzyme activity was confirmed on the collected fractions numbered from 7 to 10. Further, it was considered from the results of SDS-PAGE that the bands around 75 kDa, 45 kDa and 25 kDa were likely those of ethanolamine phosphate-degrading enzymes.

The fractions numbered from 7 to 10 in the above-described hydrophobic chromatography were collected, and were subjected to fractionation through a hydroxyapatite column ("HT-Gel", product of Bio-Rad Laboratories, Inc.). As eluents, a 10 mM potassium phosphate solution (pH 9.0) (Buffer E-1) and a 300 mM potassium phosphate solution (pH 9.0) (Buffer E-2) were used. Similar to the above-described anion chromatography, SDS-PAGE and absorbance measurements using the acetaldehyde quantification kit were conducted on the respective fractions. Results are shown in FIG. 4. As apparent from FIG. 4, high ethanolamine phosphate-degrading enzyme activity was confirmed on the collected fractions of numbers w and 1. Further, it was considered from the results of SDS-PAGE that the bands around 45 kDa and 25 kDa were likely those of ethanolamine phosphate-degrading enzymes.

From the results of the fractionation by the three kinds of chromatography, the three bands of 75 kDa, 45 kDa and 25 kDa were selected as candidates for ethanolamine phosphate-degrading enzymes.

In each of the experiments described above, acetaldehyde was formed by the addition of the cell lysate of *Pantoea ananatis* to the solution that contained ethanolamine phosphate. It has, therefore, been confirmed that the ethanolamine phosphate-degrading enzymes described above are enzymes capable of catalyzing the reaction of equation (1).

4. Identification of Ethanolamine Phosphate Lyase Derived from *Pantoea ananatis*

The three bands selected in Item 3 described above were collected from the SDS-PAGE gel, and the determination of their amino acid sequences was contracted to a custom service provider (Hokkaido System Science Co., Ltd.). As a result, those bands were all recognized to have high homology with the below-described proteins, respectively, and from their molecular weights and N-terminal amino acid sequences, were also confirmed to correspond to the following proteins, respectively.

75 kDa: phenylalanyl-tRNA synthesis enzyme, β-subunit (*Pantoea vagans* C9-1)
45 kDa: GabT (*Pantoea ananatis* LMG20103) shown as SEQ ID NO:1
25 kDa: WrbA (*Pantoea ananatis* LMG20103)

Among the above-described proteins, the phenylalanyl-tRNA synthesis enzyme and WrbA have been reported to catalyze reactions different from deamination and dephosphorylation. They were, accordingly, excluded from the candidates for ethanolamine phosphate-degrading enzymes.

The remaining gene for GabT has been confirmed to exist in the genomes of a relatively small number of microorganism species, plants, and animals such as human. In animals, its expression in the brain has been reported. As a function of GabT, GabT is known to transfer an amino group from γ-aminobutyric acid (GABA) as a substrate to an organic acid in a pyridoxal phosphate-dependent manner.

Further, GabT has also been reported to have transamination (deamination) activity for a relatively broad range of substrates other than GABA, and with GabT derived from *E. coli*, transamination activity for 3-aminopropyl(methyl) phosphinic acid similar in structure to ethanolamine phosphate has been reported. The ethanolamine phosphate degradation reaction of the equation (1) is accompanied by dephosphorylation, and therefore, is different from known reaction modes of GabT. In view of the above-described similarity, however, GabT has been determined to have a high possibility of being an enzyme that catalyzes the reaction of equation (1).

5. Cloning of *Pantoea ananatis* gabT Gene and *E. coli* gabT Gene

A band corresponding to the gabT gene was obtained from the genome of *Pantoea ananatis* by a known PCR-dependent cloning method, and was ligated to pUC18 for amplification. A DNA sequence analysis was contracted to a custom service provider (Hokkaido System Science Co., Ltd.), and the target gabT gene was confirmed to be obtained. The amino acid sequence of the resulting *Pantoea ananatis*-derived GabT is shown as SEQ ID NO:1 in the accompanying sequence listing.

Similarly, from *E. coli* (wt) in the genome of which the existence of the gabT gene has been confirmed, the genome was extracted, a band corresponding to the gabT gene was obtained by a known cloning method, and the band was ligated to pUC18 for amplification. As a result of a DNA sequence analysis, the target gabT gene was confirmed to be obtained. The amino acid sequence of the resulting *E. coli*-derived GabT is shown as SEQ ID NO:2 in the accompanying sequence listing, and the base sequence of the *E. coli*-derived gabT gene is shown as SEQ ID NO:3.

6. Construction of GabT Expression System and Confirmation of Enzyme Activity

Referential Example 5

The *Pantoea ananatis*-derived gabT gene, an expression product of which will be abbreviated as P-GabT", was inserted in the expression vector pET23a to transform the *E. coli* BL21(DE3) strain. The transformed *E. coli* was cultured in LB medium, and IPTG was added in a presteady state to induce the expression of P-GabT. Five hours after the induction, centrifugation was conducted to harvest cells. The thus-obtained cells were suspended in a lysis buffer with pyridoxal phosphate contained therein (10 mM pyridoxal phosphate, 100 mM potassium chloride, 1 mM ethylenediaminetetraacetic acid, 100 mM potassium chloride, 1 mM dithiothreitol, 50 mM tris-hydrochloric acid, pH 7.5), and then, cell disruption was conducted by sonication.

The resulting cell lysate was centrifuged to collect a supernatant fraction. The cell lysate before the centrifugation, which will be abbreviated as "total", and the supernatant fraction, which will be abbreviated as "sup", were separately added to portions of a tris-hydrochloric acid buffer (final concentration: 20 mM: pH 7.5) containing ethanolamine phosphate (final concentration: 1 mM) and pyridoxal phosphate (final concentration: 1 mM) such that their final volume ratios reached 30%. After the resulting mixtures were separately subjected to the reaction at 30° C., acetaldehyde dehydrogenase (ALDH) and oxidized nicotinamide dehydrogenase (NAD$^+$) were added to the respective samples after the reaction according to the manual of the commercial acetaldehyde quantification kit ("F-kit Acetaldehyde", product of Roche Diagnostics K.K.). Subsequent to the reaction of equation (2), the absorbances at 340 nm were measured. From each absorbance, the acetaldehyde in the corresponding sample after the react ion of equation (1) was quantified, and the ethanolamine phosphate-degrading enzyme activity in the sample before the reaction of equation (1) was determined on the basis of acetaldehyde level. Results are indicated by "P-" in FIG. 5. In the graph, the ordinate indicates the absorbance at 340 nm, and each error bar indicates a standard deviation obtained from thrice repeated measurements.

Referential Example 6

By similar methods and procedures as in Referential Example 5 except for the use of *E. coli*-derived gabT gene (an expression product of which will be abbreviated as "E-GabT") in place of the *Pantoea ananatis*-derived gabT gene, an experiment was conducted to obtain a cell lysate and supernatant fraction. Their ethanolamine phosphate-degrading enzyme activities were measured. Results are indicated by "E-" in FIG. 5.

Referential Example 7

By similar methods and procedures as in Referential Example 5 except that the transformation was conducted using pET23a alone as a negative control, an experiment was conducted. The ethanolamine phosphate-degrading enzyme activities of a cell lysate and supernatant fraction were measured. Results are indicated by "NC" in FIG. 5.

From the results of Referential Examples 5 to 7, in the case of the cell lysates on a left side in FIG. 5, it was possible to confirm high ethanolamine phosphate-degrading enzyme activity on both P-GabT and E-GabT compared with the negative control. In the case of the supernatant fractions on a right side in FIG. 5, on the other hand, both P-GabT and E-GabT had similar enzyme activity as the negative control. Further, also in SDS-PAGE, P-GabT and E-GabT were both confirmed as dark bands at 45 kDa in the case of the cell lysates, but were of similar levels as the control in the case of the supernatant fractions (not shown). From the above results, P-GabT and E-GabT are both considered to exist as inclusion bodies in the precipitate fractions.

7. Determination of Sequences of GabT Domains

Referential Example 8

The amino acid sequences of GabTs (aminobutyric acid aminotransferase in the case of mammals) derived from *Sulfolobus* (*Sulfolobus tokodaii* str. 7; SEQ ID NO: 4) as an archaebacteria, human (*Homo sapiens*; SEQ ID NO: 5) and mouse (*Mus musculus*; SEQ ID NO: 6) as the mammals, and *Arabidopsis* (*Arabidopsis thaliana*; SEQ ID NO: 7) as a plant, in addition to *Pantoea ananatis* and *E. coli* used in Referential Examples 5 to 7, were aligned using a commercial program ("CLC Sequence Viewer", prepared by CLC Bio Japan, Inc.). Results are shown in FIG. 6. In FIG. 6, the region boxed by a thick line and containing the $301^{st}$ to $317^{th}$ amino acids was extracted as a region of high conservation. It is to be noted that the amino acids shown in rows labeled "consensus" are residues conserved 60% or more.

Referential Example 9

In addition to the GabT sequences of the above-described six organism species, *Salmonella* (*Salmonella enterica* subsp. *enterica* serovar *Typhi* strain CT18), *Clostridium* (*Clostridium acetobutylicum* ATCC 824), *Pseudomonas* (*Pseudomonas putida* KT2440), *Rhodococcus* (*Rhodococcus equi* 103S), *Acinetobacter* (*Acinetobacter baumanii* ACICU), *Mycobacter* (*Mycobacterium avium* subsp. *paratuberculosis* K-10), cattle (*Bos taurus*), larvacea (*Oikopleura dioica*), maize (*Zea mays*) and red pepper (*Capsicum annuum*) were also verified for the conservation of the domain regions specified in Referential Example 8. Concerning the amino acid sequence ranging from the $301^{st}$ to the $317^{th}$, at least 90% of homology was conserved in the above-described 16 organism species. This region was, therefore, defined as a GabT domain.

The GabT domain is an amino acid sequence region consisting of the following amino acid sequence:

GXXXBADEBQXGFZRXG wherein X means an amino acid, B denotes a branched amino acid selected from the group consisting of I, L and V, and Z signifies G or A. The sequences of the GabT domains of the respective organism species are shown in Table 1. In the sequences of Table 1, those different from the corresponding amino acids in the GabT domain defined as described above are indicated by underlining them.

TABLE 1

| Organism name/organism species | Sequence | Homology (%) | SEQ ID NO: |
|---|---|---|---|
| Pantoea / Pantoea ananatis LMG 20103 | GIMLICDEIQSGFGRTG | 91 | 8 |
| E. coli / Escherichia coli str. K-12 substr. MG1655 | GIMLIADEVQSGAGRTG | 91 | 9 |
| Sulfolobus / Sulfolobus tokodaii str. 7 | GILLVDDEVQMGLGRTG | 91 | 10 |
| Salmonella / Salmonella enterica subsp. enterica serovar Typhi str. CT18 | GIMLIADEVQSGAGRTG | 91 | 11 |
| Clostridium / Clostridium acetobutylicum ATCC 824 | DIVFIIDEVQAGFGRTG | 91 | 12 |
| Pseudomonas / Pseudomonas putida KT2440 | GILLIADEVQTGAGRTG | 91 | 13 |
| Rhodococcus / Rhodococcus equi 103S | GIVFVADEVQTGFARTG | 100 | 14 |
| Acinetobacter / Acinetobacterbaumannii ACICU | GILLVADEVQSGFARTG | 100 | 15 |
| Mycobacter / Mycobacterium avium subsp. paratuberculosis K-10 | DVLFIADEVQTGFARSG | 91 | 16 |
| Human / Homo sapiens | GGVFIADEVQVGFGRVG | 100 | 17 |
| Bovine / Bos taurus | GGVFIADEVQVGFGRVG | 100 | 18 |
| Mouse / Mus musculus | GGLFVADEIQVGFGRIG | 100 | 19 |
| Ascidian / Oikopleura dioica | GVLTIADEVQVGFGRVG | 100 | 20 |
| Thale cress / Arabidopsis thaliana | GGVCIADEVQTGFGRTG | 100 | 21 |
| Corn / Zea mays | GGLCIADEVQAGFARVG | 100 | 22 |
| Cayenne / Capsicum annuum | GGVCIADEVQTGFGRTG | 100 | 23 |

The invention claimed is:

1. A composition for screening a human patient having depression, comprising:
   a plasma sample of a human subject; and
   an ethanolamine phosphate-measuring reagent comprising an enzyme that catalyzes a reaction that forms acetaldehyde from ethanolamine phosphate,
   wherein the enzyme is a protein having an amino acid sequence region having at least 90% of homology with a GabT domain consisting of a following amino acid sequence:

GXXXBADEBQXGFZRXG wherein X means an amino acid, B denotes a branched amino acid selected from the group consisting of I, L, and V, and Z signifies G or A, and
   the enzyme is derived from at least one source material selected from the group consisting of *Pantoea, E. coli, Sulfolobus, Arabidopsis, Salmonella, Clostridium, Pseudomonas, Rhodococcus, Acinetobacter, Mycobacter*, cattle, mice, larvacea, maize, and red peppers.

2. The composition according to claim 1, wherein the enzyme is:
   (1) a protein consisting of an amino acid sequence represented by SEQ ID NO:1 or 2,
   (2) a protein consisting of an amino acid sequence that in the amino acid sequence represented by SEQ ID NO:1 or 2 one or a few amino acids have been deleted, substituted, or added, or
   (3) a protein consisting of an amino acid sequence having at least 90% of homology with the amino acid sequence represented by SEQ ID NO:1 or 2.

3. The composition according to claim 1, further comprising a coenzyme for the enzyme.

4. The composition according to claim 3, wherein the coenzyme is pyridoxal phosphate.

5. The composition according to claim 1, wherein the enzyme is derived from *Pantoea ananatis*.

6. A composition for determining whether a human patient has depression, comprising:
   a plasma sample of the human patient; and
   an ethanolamine phosphate-measuring reagent comprising an enzyme that catalyzes a reaction that forms acetaldehyde from ethanolamine phosphate,
   wherein the enzyme is a protein having an amino acid sequence region having at least 90% of homology with a GabT domain consisting of a following amino acid sequence:

GXXXBADEBQXGFZRXG wherein X means an amino acid, B denotes a branched amino acid selected from the group consisting of I, L, and V, and Z signifies G or A, and
   the enzyme is derived from at least one source material selected from the group consisting of *Pantoea, E. coli, Sulfolobus, Arabidopsis, Salmonella, Clostridium, Pseudomonas, Rhodococcus, Acinetobacter, Mycobacter*, cattle, mice, larvacea, maize, and red peppers.

7. The composition according to claim 6, wherein the enzyme is derived from *Pantoea ananatis*.

\* \* \* \* \*

SEQUENCE LISTING

<160> NUMBER OF SEQ ID NOS: 23

<210> SEQ ID NO 1
<211> LENGTH: 438
<212> TYPE: PRT
<213> ORGANISM: Pantoea ananatis LMG 20103
<220> FEATURE:
<223> OTHER INFORMATION: Ethanolamine phosphate catabolic enzyme

<400> SEQUENCE: 1

Met Gln Asn Val Leu Ala Glu Gln Gln Thr Tyr Ala Asp Asn Ser Gln
1               5                   10                  15

Leu Leu Asp Val Arg Asp His Asn Val Pro Arg Gly Ile Ile Thr Ala
            20                  25                  30

His Pro Leu Val Ile Glu Arg Ala Lys Gly Ser Glu Val Trp Asp Val
        35                  40                  45

Glu Gly Asn Arg Tyr Leu Asp Phe Val Gly Gly Ile Gly Val Leu Asn
    50                  55                  60

Val Gly His Asn His Pro Ala Val Val Asn Ala Val Thr Arg Gln Leu
65                  70                  75                  80

Gly Met Val Ser His Ala Cys Phe Gln Val Ala Ala Tyr Pro Gly Tyr
                85                  90                  95

Ile Glu Leu Ala Gln Arg Leu Asn Lys Leu Val Gly Gly Asp Glu His
            100                 105                 110

Tyr Lys Ser Val Phe Phe Thr Ser Gly Ala Glu Ala Val Glu Asn Ala
        115                 120                 125

Val Lys Ile Ala Arg Ser Tyr Thr Gln Arg Pro Gly Ile Ala Phe
            130                 135                 140

Asp Gly Ala Phe His Gly Arg Thr Leu Leu Gly Val Thr Leu Thr Gly
145                 150                 155                 160

Met Ser Ala Pro Tyr Lys Gln Asn Phe Gly Pro Phe Pro Gly Asp Val
                165                 170                 175

Tyr Arg Leu Pro Phe Pro Asn Pro Leu His Gly Val Thr Glu Ala Asp
            180                 185                 190

Cys Leu Lys Ala Leu Asp Gln Leu Phe Ser Val Gln Ile Leu Pro Glu
            195                 200                 205

Arg Val Ala Ala Ile Ile Ile Glu Pro Val Gln Gly Asp Gly Gly Phe
            210                 215                 220

Leu Pro Ala Gly Pro Ala Phe Met Gln Ala Leu Arg Arg Ile Thr Thr
225                 230                 235                 240

Gln His Gly Ile Met Leu Ile Cys Asp Glu Ile Gln Ser Gly Phe Gly
                245                 250                 255

Arg Thr Gly Thr Met Phe Ala Phe Gln Gln Leu Gly Ile Lys Pro Asp
            260                 265                 270

Met Ile Thr Thr Ala Lys Ser Leu Ala Gly Gly Leu Pro Ile Ser Gly
            275                 280                 285

Val Val Gly Lys Ala Glu Ile Met Asp Ser Pro Ala Pro Gly Gly Leu
290                 295                 300

Gly Gly Thr Tyr Gly Gly Asn Ala Leu Ala Cys Ala Ala Ala Leu Ala
305                 310                 315                 320

Val Leu Asp Ile Phe Glu Gln Glu Asn Leu Leu Ala Arg Ser Cys Gln
                325                 330                 335

Leu Gly Glu Gln Leu Asn Gln Arg Leu Arg Gln Leu Ala Asp Lys Tyr
            340                 345                 350

Ala Cys Ile Gly Asp Val Arg Gly Val Gly Phe Met Gln Ala Val Glu
            355                 360                 365

Ile Leu Asp Val Asp Thr His Lys Pro Asp Ser Ala Leu Thr Gln Lys
            370                 375                 380

Ile Leu Asp Ser Ala Cys Gln Glu Gly Leu Leu Leu Ile Lys Cys Gly
385                 390                 395                 400

Leu His Arg Asn Thr Ile Arg Phe Leu Ala Pro Leu Val Thr Thr Asp
                405                 410                 415

Ser Gln Leu Glu Glu Ala Leu His Ile Phe Asp Ile Ala Leu Ala Arg
            420                 425                 430

Ala Thr Gly Arg Leu Gly
            435

<210> SEQ ID NO 2
<211> LENGTH: 426
<212> TYPE: PRT
<213> ORGANISM: Escherichia coli str. K-12 substr. MG1655
<220> FEATURE:
<223> OTHER INFORMATION: Ethanolamine phosphate catabolic enzyme

<400> SEQUENCE: 2

Met Asn Ser Asn Lys Glu Leu Met Gln Arg Ser Gln Ala Ile Pro
1               5                   10                  15

Arg Gly Val Gly Gln Ile His Pro Ile Phe Ala Asp Arg Ala Glu Asn
            20                  25                  30

Cys Arg Val Trp Asp Val Glu Gly Arg Glu Tyr Leu Asp Phe Ala Gly
            35                  40                  45

```
Gly Ile Ala Val Leu Asn Thr Gly His Leu His Pro Lys Val Ala
     50                  55                  60

Ala Val Glu Ala Gln Leu Lys Lys Leu Ser His Thr Cys Phe Gln Val
 65              70                  75                  80

Leu Ala Tyr Glu Pro Tyr Leu Glu Leu Cys Glu Ile Met Asn Gln Lys
                 85                  90                  95

Val Pro Gly Asp Phe Ala Lys Lys Thr Leu Leu Val Thr Thr Gly Ser
                100                 105                 110

Glu Ala Val Glu Asn Ala Val Lys Ile Ala Arg Ala Ala Thr Lys Arg
            115                 120                 125

Ser Gly Thr Ile Ala Phe Ser Gly Ala Tyr His Gly Arg Thr His Tyr
    130                 135                 140

Thr Leu Ala Leu Thr Gly Lys Val Asn Pro Tyr Ser Ala Gly Met Gly
145                 150                 155                 160

Leu Met Pro Gly His Val Tyr Arg Ala Leu Tyr Pro Cys Pro Leu His
                165                 170                 175

Gly Ile Ser Glu Asp Asp Ala Ile Ala Ser Ile His Arg Ile Phe Lys
                180                 185                 190

Asn Asp Ala Ala Pro Glu Asp Ile Ala Ala Ile Ile Glu Pro Val
                195                 200                 205

Gln Gly Glu Gly Gly Phe Tyr Ala Ser Ser Pro Ala Phe Met Gln Arg
    210                 215                 220

Leu Arg Ala Leu Cys Asp Glu His Gly Ile Met Leu Ile Ala Asp Glu
225                 230                 235                 240

Val Gln Ser Gly Ala Gly Arg Thr Gly Thr Leu Phe Ala Met Glu Gln
                245                 250                 255

Met Gly Val Ala Pro Asp Leu Thr Thr Phe Ala Lys Ser Ile Ala Gly
                260                 265                 270

Gly Phe Pro Leu Ala Gly Val Thr Gly Arg Ala Glu Val Met Asp Ala
            275                 280                 285

Val Ala Pro Gly Gly Leu Gly Gly Thr Tyr Ala Gly Asn Pro Ile Ala
    290                 295                 300

Cys Val Ala Ala Leu Glu Val Leu Lys Val Phe Glu Gln Glu Asn Leu
305                 310                 315                 320

Leu Gln Lys Ala Asn Asp Leu Gly Gln Lys Leu Lys Asp Gly Leu Leu
                325                 330                 335

Ala Ile Ala Glu Lys His Pro Glu Ile Gly Asp Val Arg Gly Leu Gly
                340                 345                 350

Ala Met Ile Ala Ile Glu Leu Phe Glu Asp Gly Asp His Asn Lys Pro
    355                 360                 365

Asp Ala Lys Leu Thr Ala Glu Ile Val Ala Arg Ala Arg Asp Lys Gly
370                 375                 380

Leu Ile Leu Leu Ser Cys Gly Pro Tyr Tyr Asn Val Leu Arg Ile Leu
385                 390                 395                 400

Val Pro Leu Thr Ile Glu Asp Ala Gln Ile Arg Gln Gly Leu Glu Ile
                405                 410                 415

Ile Ser Gln Cys Phe Asp Glu Ala Lys Gln
                420                 425

<210> SEQ ID NO 3
<211> LENGTH: 1281
<212> TYPE: DNA
<213> ORGANISM: Escherichia coli
<220> FEATURE:
```

<223> OTHER INFORMATION: E. coli str. K-12 substr. MG1655 chromosome

<400> SEQUENCE: 3

```
atgaacagca ataaagagtt aatgcagcgc cgcagtcagg cgattccccg tggcgttggg      60
caaattcacc cgattttcgc tgaccgcgcg gaaaaactgcc gggtgtggga cgttgaaggc    120
cgtgagtatc ttgatttcgc gggcgggatt gcggtgctca ataccgggca cctgcatccg    180
aaggtggtgg ccgcggtgga agcgcagttg aaaaaactgt cgcacacctg cttccaggtg    240
ctggcttacg agccgtatct ggagctgtgc gagattatga atcagaaggt gccgggcgat    300
ttcgccaaga aaacgctgct ggttacgacc ggttccgaag cggtggaaaa cgcggtaaaa    360
atcgcccgcg ccgccaccaa cgtagcggc accatcgctt tagcggcgc gtatcacggg      420
cgcacgcatt acacgctggc gctgaccggc aaggtgaatc cgtactctgc gggcatgggg    480
ctgatgccgg tcatgtttta cgcgcgctt tatccttgcc cgctgcacgg cataagcgag    540
gatgacgcta cgccagcat ccaccggatc ttcaaaaatg atgccgcgcc ggaagatatc    600
gccgccatcg tgattgagcc ggttcaggcg gaaggcggtt tctacgcctc gtcgccagcc    660
tttatgcagc gtttacgcgc tctgtgtgac gagcacggga tcatgctgat tgccgatgaa    720
gtgcagagcg gcgcggggcg taccggcacg ctgtttgcga tggagcagat gggcgttgcg    780
ccggatctta ccacctttgc gaaatcgatc gcgggcggct tccgctggc gggcgtcacc    840
gggcgcgcg aagtaatgga tgccgtcgct ccaggcggtc tgggcggcac ctatgcgggt    900
aacccgattg cctgcgtggc tgcgctggaa gtgttgaagg tgtttgagca ggaaaatctg    960
ctgcaaaaag ccaacgatct gggcgagaag ttgaaagacg gattgctggc gatagccgaa    1020
aaacacccgg agatcggcga cgtacgcggg ctgggggcga tgatcgccat tgagctgttt    1080
gaagacggcg atcacaacaa gccggacgcc aaactcaccg ccgagatcgt ggctcgcgcc    1140
cgcgataaag gcctgattct tctctcctgc ggcccgtatt acaacgtgct gcgcatcctt    1200
gtaccgctca ccattgaaga cgctcagatc cgtcagggtc tggagatcat cagccagtgt    1260
tttgatgagg cgaagcagta g                                                1281
```

<210> SEQ ID NO 4
<211> LENGTH: 419
<212> TYPE: PRT
<213> ORGANISM: Sulfolobus tokodaii str. 7

<400> SEQUENCE: 4

```
Met Leu Ser Arg Lys Ile Ile Glu Glu Ser Asp Ile Tyr Leu Ala Thr
1               5                   10                  15

Ser Thr Arg Asp Pro Glu Leu Phe Pro Leu Val Ile Asp His Gly Glu
            20                  25                  30

Gly Val Trp Ile Tyr Asp Val Asp Gly Asn Lys Tyr Leu Asp Phe Thr
        35                  40                  45

Ser Gly Ile Gly Val Asn Asn Leu Gly Trp Pro Ser His Pro Glu Val
    50                  55                  60

Ile Lys Ile Gly Ile Glu Gln Met Gln Lys Leu Ala His Ala Ala
65                  70                  75                  80

Asn Asp Phe Tyr Asn Ile Pro Gln Leu Glu Leu Ala Lys Lys Leu Val
                85                  90                  95

Thr Tyr Ser Pro Gly Asn Phe Gln Lys Lys Val Phe Phe Ser Asn Ser
            100                 105                 110

Gly Thr Glu Ala Ile Glu Ala Ser Ile Lys Val Val Lys Asn Thr Gly
        115                 120                 125
```

```
Arg Lys Tyr Ile Ile Ala Phe Leu Gly Gly Phe His Gly Arg Thr Phe
    130                 135                 140

Gly Ser Ile Ser Leu Thr Ala Ser Lys Ala Val Gln Arg Ser Ile Val
145                 150                 155                 160

Gly Pro Phe Met Pro Gly Val Ile His Val Pro Tyr Pro Asn Pro Tyr
                165                 170                 175

Arg Asn Pro Trp His Ile Asn Gly Tyr Glu Asn Pro Ser Glu Leu Val
                180                 185                 190

Asn Arg Val Ile Glu Phe Ile Glu Asp Tyr Ile Phe Val Asn Leu Val
            195                 200                 205

Pro Pro Glu Glu Val Ala Gly Ile Phe Phe Pro Ile Gln Gly Glu
    210                 215                 220

Gly Gly Tyr Val Ile Pro Pro Lys Asn Phe Phe Ala Glu Leu Gln Lys
225                 230                 235                 240

Leu Ala Lys Lys Tyr Gly Ile Leu Leu Val Asp Asp Glu Val Gln Met
                245                 250                 255

Gly Leu Gly Arg Thr Gly Lys Leu Phe Ala Ile Glu Asn Phe Asn Thr
            260                 265                 270

Val Pro Asp Val Ile Thr Leu Ala Lys Ala Leu Gly Gly Gly Ile Met
    275                 280                 285

Pro Ile Gly Ala Thr Ile Phe Arg Lys Asp Leu Asp Phe Lys Pro Gly
    290                 295                 300

Met His Ser Asn Thr Phe Gly Gly Asn Ala Leu Ala Cys Ala Ile Gly
305                 310                 315                 320

Ser Lys Val Ile Asp Ile Val Lys Asp Leu Leu Pro His Val Asn Glu
                325                 330                 335

Ile Gly Lys Ile Phe Ala Glu Glu Leu Gln Gly Leu Ala Asp Asp Val
            340                 345                 350

Arg Gly Ile Gly Leu Ala Trp Gly Leu Glu Tyr Asn Glu Lys Lys Val
            355                 360                 365

Arg Asp Arg Ile Ile Gly Glu Ser Phe Lys Arg Gly Leu Leu Leu Leu
    370                 375                 380

Pro Ala Gly Arg Ser Ala Ile Arg Val Ile Pro Pro Leu Val Ile Ser
385                 390                 395                 400

Glu Glu Glu Ala Lys Gln Gly Leu Asp Ile Leu Lys Lys Val Ile Lys
                405                 410                 415

Val Val Lys

<210> SEQ ID NO 5
<211> LENGTH: 499
<212> TYPE: PRT
<213> ORGANISM: Homo sapiens

<400> SEQUENCE: 5

Met Cys Glu Leu Tyr Ser Lys Arg Asp Thr Leu Gly Leu Arg Lys Lys
1               5                   10                  15

His Ile Gly Pro Ser Cys Lys Val Phe Phe Ala Ser Asp Pro Ile Lys
                20                  25                  30

Ile Val Arg Ala Gln Arg Gln Tyr Met Phe Asp Glu Asn Gly Glu Gln
            35                  40                  45

Tyr Leu Asp Cys Ile Asn Asn Val Ala His Val Gly His Cys His Pro
    50                  55                  60

Gly Val Val Lys Ala Ala Leu Lys Gln Met Glu Leu Leu Asn Thr Asn
65                  70                  75                  80
```

```
Ser Arg Phe Leu His Asp Asn Ile Val Glu Tyr Ala Lys Arg Leu Ser
                85                  90                  95

Ala Thr Leu Pro Glu Lys Leu Ser Val Cys Tyr Phe Thr Asn Ser Gly
            100                 105                 110

Ser Glu Ala Asn Asp Leu Ala Leu Arg Leu Ala Arg Gln Phe Arg Gly
        115                 120                 125

His Gln Asp Val Ile Thr Leu Asp His Ala Tyr His Gly His Leu Ser
130                 135                 140

Ser Leu Ile Glu Ile Ser Pro Tyr Lys Phe Gln Lys Gly Lys Asp Val
145                 150                 155                 160

Lys Lys Glu Phe Val His Val Ala Pro Thr Pro Asp Thr Tyr Arg Gly
                165                 170                 175

Lys Tyr Arg Glu Asp His Ala Asp Ser Ala Ser Ala Tyr Ala Asp Glu
            180                 185                 190

Val Lys Lys Ile Ile Glu Asp Ala His Asn Ser Gly Arg Lys Ile Ala
        195                 200                 205

Ala Phe Ile Ala Glu Ser Met Gln Ser Cys Gly Gly Gln Ile Ile Pro
210                 215                 220

Pro Ala Gly Tyr Phe Gln Lys Val Ala Glu Tyr Val His Gly Ala Gly
225                 230                 235                 240

Gly Val Phe Ile Ala Asp Glu Val Gln Val Gly Phe Gly Arg Val Gly
                245                 250                 255

Lys His Phe Trp Ser Phe Gln Met Tyr Gly Glu Asp Phe Val Pro Asp
            260                 265                 270

Ile Val Thr Met Gly Lys Pro Met Gly Asn Gly His Pro Val Ala Cys
        275                 280                 285

Val Val Thr Thr Lys Glu Ile Ala Glu Ala Phe Ser Ser Ser Gly Met
290                 295                 300

Glu Tyr Phe Asn Thr Tyr Gly Gly Asn Pro Val Ser Cys Ala Val Gly
305                 310                 315                 320

Leu Ala Val Leu Asp Ile Ile Glu Asn Glu Asp Leu Gln Gly Asn Ala
                325                 330                 335

Lys Arg Val Gly Asn Tyr Leu Thr Glu Leu Leu Lys Lys Gln Lys Ala
            340                 345                 350

Lys His Thr Leu Ile Gly Asp Ile Arg Gly Ile Gly Leu Phe Ile Gly
        355                 360                 365

Ile Asp Leu Val Lys Asp His Leu Lys Arg Thr Pro Ala Thr Ala Glu
370                 375                 380

Ala Gln His Ile Ile Tyr Lys Met Lys Glu Lys Arg Val Leu Leu Ser
385                 390                 395                 400

Ala Asp Gly Pro His Arg Asn Val Leu Lys Ile Lys Pro Pro Met Cys
                405                 410                 415

Phe Thr Glu Glu Asp Ala Lys Phe Met Val Asp Gln Leu Asp Arg Ile
            420                 425                 430

Leu Thr Val Leu Glu Glu Ala Met Gly Thr Lys Thr Glu Ser Val Thr
        435                 440                 445

Ser Glu Asn Thr Pro Cys Lys Thr Lys Met Leu Lys Glu Ala His Ile
450                 455                 460

Glu Leu Leu Arg Asp Ser Thr Thr Asp Ser Lys Glu Asn Pro Ser Arg
465                 470                 475                 480

Lys Arg Asn Gly Met Cys Thr Asp Thr His Ser Leu Leu Ser Lys Arg
                485                 490                 495
```

Leu Lys Thr

<210> SEQ ID NO 6
<211> LENGTH: 467
<212> TYPE: PRT
<213> ORGANISM: Mus musculus

<400> SEQUENCE: 6

Met Ala Ala Asp Thr Arg Ala Lys Ala Val Thr Leu Asp Leu Arg Arg
1               5                   10                  15

Arg Leu Leu Ser Ser Cys Arg Leu Phe Phe Pro Glu Asp Pro Val
                20                  25                  30

Lys Ile Ile Arg Gly Gln Gly Gln Tyr Leu Tyr Asp Glu Gln Gly Arg
            35                  40                  45

Glu Tyr Leu Asp Cys Ile Asn Asn Val Ala His Val Gly His Cys His
        50                  55                  60

Pro Thr Val Val Gln Ala Ala His Glu Gln Asn Leu Val Leu Asn Thr
65                  70                  75                  80

Asn Ser Arg Tyr Leu His Asp Asn Ile Val Asp Tyr Ala Gln Arg Leu
                85                  90                  95

Ser Glu Thr Leu Pro Glu Gln Leu Ser Val Phe Tyr Phe Leu Asn Ser
                100                 105                 110

Gly Ser Glu Ala Asn Asp Leu Ala Leu Arg Leu Ala Arg Gln Tyr Thr
            115                 120                 125

Gly His Gln Asp Val Val Leu Asp His Ala Tyr His Gly His Leu
        130                 135                 140

Ser Ser Leu Ile Asp Ile Ser Pro Tyr Lys Phe Arg Asn Leu Gly Gly
145                 150                 155                 160

Gln Lys Glu Trp Val His Val Ala Pro Leu Pro Asp Thr Tyr Arg Gly
                165                 170                 175

Pro Tyr Arg Glu Asp His Pro Asn Pro Ala Glu Ala Tyr Ala Asn Glu
                180                 185                 190

Val Lys His Val Ile Ser Ser Ala Gln Gln Lys Gly Arg Lys Ile Ala
            195                 200                 205

Ala Phe Phe Ala Glu Ser Leu Pro Ser Val Ser Gly Gln Ile Ile Pro
        210                 215                 220

Pro Ala Gly Tyr Phe Ser Gln Val Ala Glu His Ile His Arg Ala Gly
225                 230                 235                 240

Gly Leu Phe Val Ala Asp Glu Ile Gln Val Gly Phe Gly Arg Ile Gly
                245                 250                 255

Lys His Phe Trp Ala Phe Gln Leu Glu Gly Glu Asp Phe Val Pro Asp
                260                 265                 270

Ile Val Thr Met Gly Lys Ser Ile Gly Asn Gly His Pro Val Ala Cys
            275                 280                 285

Met Ala Thr Thr Gln Ala Val Ser Arg Ala Phe Glu Ala Thr Gly Val
        290                 295                 300

Glu Tyr Phe Asn Thr Phe Gly Gly Asn Pro Val Ser Cys Ala Val Gly
305                 310                 315                 320

Leu Ala Val Leu Asp Val Leu Lys Thr Glu Gln Leu Gln Ala His Ala
                325                 330                 335

Thr Asn Val Gly Ser Phe Leu Leu Glu His Leu Thr Gln Gln Lys Ala
            340                 345                 350

Lys His Pro Ile Ile Gly Asp Val Arg Gly Thr Gly Leu Phe Ile Gly
        355                 360                 365

```
Val Asp Leu Ile Lys Asp Glu Thr Leu Arg Thr Pro Ala Thr Glu Glu
    370                 375                 380

Ala Glu Tyr Leu Val Ser Arg Leu Lys Glu Asn Tyr Ile Leu Leu Ser
385                 390                 395                 400

Ile Asp Gly Pro Gly Lys Asn Ile Leu Lys Phe Lys Pro Pro Met Cys
                405                 410                 415

Phe Asn Val Asp Asn Ala Gln His Val Val Ala Lys Leu Asp Asp Ile
            420                 425                 430

Leu Thr Asp Met Glu Glu Lys Val Arg Ser Cys Glu Thr Leu Arg Ile
        435                 440                 445

Lys His Pro Pro Glu Asp Thr His Pro Thr Gln Ile Leu Leu Thr Arg
    450                 455                 460

Gln Gln Asp
465

<210> SEQ ID NO 7
<211> LENGTH: 476
<212> TYPE: PRT
<213> ORGANISM: Arabidopsis thaliana

<400> SEQUENCE: 7

Met Ala Leu Gln Arg Gln Leu Leu Lys Arg Ala Thr Ser Asp Ile Tyr
1               5                   10                  15

His Arg Arg Ala Ile Ser Leu Leu Arg Thr Asp Phe Ser Thr Ser Pro
            20                  25                  30

Ser Ile Ala Asp Ala Pro Pro His Ile Pro Pro Phe Val His Gln Pro
        35                  40                  45

Arg Pro Tyr Lys Gly Pro Ser Ala Asp Glu Val Leu Gln Lys Arg Lys
    50                  55                  60

Lys Phe Leu Gly Pro Ser Leu Phe His Tyr Tyr Gln Lys Pro Leu Asn
65                  70                  75                  80

Ile Val Glu Gly Lys Met Gln Tyr Leu Tyr Asp Glu Ser Gly Arg Arg
                85                  90                  95

Tyr Leu Asp Ala Phe Ala Gly Ile Val Thr Val Ser Cys Gly His Cys
            100                 105                 110

His Pro Asp Ile Leu Asn Ala Ile Thr Glu Gln Ser Lys Leu Leu Gln
        115                 120                 125

His Ala Thr Thr Ile Tyr Leu His His Ala Ile Gly Asp Phe Ala Glu
    130                 135                 140

Ala Leu Ala Ala Lys Met Pro Gly Asn Leu Lys Val Val Tyr Phe Val
145                 150                 155                 160

Asn Ser Gly Ser Glu Ala Asn Glu Leu Ala Met Met Met Ala Arg Leu
                165                 170                 175

Tyr Thr Gly Ser Leu Glu Met Ile Ser Leu Arg Asn Ala Tyr His Gly
            180                 185                 190

Gly Ser Ser Asn Thr Ile Gly Leu Thr Ala Leu Asn Thr Trp Lys Tyr
        195                 200                 205

Pro Leu Pro Gln Gly Glu Ile His His Val Asn Pro Asp Pro Tyr
    210                 215                 220

Arg Gly Val Phe Gly Ser Asp Gly Ser Leu Tyr Ala Lys Asp Val His
225                 230                 235                 240

Asp His Ile Glu Tyr Gly Thr Ser Gly Lys Val Ala Gly Phe Ile Ala
                245                 250                 255

Glu Thr Ile Gln Gly Val Gly Gly Ala Val Glu Leu Ala Pro Gly Tyr
            260                 265                 270
```

```
Leu Lys Ser Val Tyr Glu Ile Val Arg Asn Ala Gly Val Cys Ile
        275                 280                 285

Ala Asp Glu Val Gln Thr Gly Phe Gly Arg Thr Gly Ser His Tyr Trp
290                 295                 300

Gly Phe Gln Thr Gln Asp Val Val Pro Asp Ile Val Thr Met Ala Lys
305                 310                 315                 320

Gly Ile Gly Asn Gly Leu Pro Leu Gly Ala Val Val Thr Thr Pro Glu
                325                 330                 335

Ile Ala Ser Val Leu Ala Ser Lys Ile Leu Phe Asn Thr Phe Gly Gly
                340                 345                 350

Asn Pro Val Cys Ser Ala Gly Gly Leu Ala Val Leu Asn Val Ile Asp
                355                 360                 365

Lys Glu Lys Arg Gln Glu His Cys Ala Glu Val Gly Ser His Leu Ile
    370                 375                 380

Gln Arg Leu Lys Asp Val Gln Lys Arg His Asp Ile Ile Gly Asp Val
385                 390                 395                 400

Arg Gly Arg Gly Leu Met Val Gly Ile Glu Leu Val Ser Asp Arg Lys
                405                 410                 415

Asp Lys Thr Pro Ala Lys Ala Glu Thr Ser Val Leu Phe Glu Gln Leu
                420                 425                 430

Arg Glu Leu Gly Ile Leu Val Gly Lys Gly Gly Leu His Gly Asn Val
    435                 440                 445

Phe Arg Ile Lys Pro Pro Met Cys Phe Thr Lys Asp Asp Ala Asp Phe
450                 455                 460

Leu Val Asp Ala Leu Asp Tyr Ser Ile Ser Arg Leu
465                 470                 475

<210> SEQ ID NO 8
<211> LENGTH: 17
<212> TYPE: PRT
<213> ORGANISM: Pantoea ananatis LMG 20103

<400> SEQUENCE: 8

Gly Ile Met Leu Ile Cys Asp Glu Ile Gln Ser Gly Phe Gly Arg Thr
1               5                   10                  15

Gly

<210> SEQ ID NO 9
<211> LENGTH: 17
<212> TYPE: PRT
<213> ORGANISM: Escherichia coli str. K-12 substr. MG1655

<400> SEQUENCE: 9

Gly Ile Met Leu Ile Ala Asp Glu Val Gln Ser Gly Ala Gly Arg Thr
1               5                   10                  15

Gly

<210> SEQ ID NO 10
<211> LENGTH: 17
<212> TYPE: PRT
<213> ORGANISM: Sulfolobus tokodaii str. 7

<400> SEQUENCE: 10

Gly Ile Leu Leu Val Asp Asp Glu Val Gln Met Gly Leu Gly Arg Thr
1               5                   10                  15

Gly
```

<210> SEQ ID NO 11
<211> LENGTH: 17
<212> TYPE: PRT
<213> ORGANISM: Salmonella enterica subsp. enterica serovar Typhi str. CT18

<400> SEQUENCE: 11

Gly Ile Met Leu Ile Ala Asp Glu Val Gln Ser Gly Ala Gly Arg Thr
1               5                   10                  15

Gly

<210> SEQ ID NO 12
<211> LENGTH: 17
<212> TYPE: PRT
<213> ORGANISM: Clostridium acetobutylicum ATCC 824

<400> SEQUENCE: 12

Asp Ile Val Phe Ile Ile Asp Glu Val Gln Ala Gly Phe Gly Arg Thr
1               5                   10                  15

Gly

<210> SEQ ID NO 13
<211> LENGTH: 17
<212> TYPE: PRT
<213> ORGANISM: Pseudomonas putida KT2440

<400> SEQUENCE: 13

Gly Ile Leu Leu Ile Ala Asp Glu Val Gln Thr Gly Ala Gly Arg Thr
1               5                   10                  15

Gly

<210> SEQ ID NO 14
<211> LENGTH: 17
<212> TYPE: PRT
<213> ORGANISM: Rhodococcus equi 103S

<400> SEQUENCE: 14

Gly Ile Val Phe Val Ala Asp Glu Val Gln Thr Gly Phe Ala Arg Thr
1               5                   10                  15

Gly

<210> SEQ ID NO 15
<211> LENGTH: 17
<212> TYPE: PRT
<213> ORGANISM: Acinetobacter baumannii ACICU

<400> SEQUENCE: 15

Gly Ile Leu Leu Val Ala Asp Glu Val Gln Ser Gly Phe Ala Arg Thr
1               5                   10                  15

Gly

<210> SEQ ID NO 16
<211> LENGTH: 17
<212> TYPE: PRT
<213> ORGANISM: Mycobacterium avium subsp. paratuberculosis K-10

<400> SEQUENCE: 16

Asp Val Leu Phe Ile Ala Asp Glu Val Gln Thr Gly Phe Ala Arg Ser
1               5                   10                  15

Gly

```
<210> SEQ ID NO 17
<211> LENGTH: 17
<212> TYPE: PRT
<213> ORGANISM: Homo sapiens

<400> SEQUENCE: 17

Gly Gly Val Phe Ile Ala Asp Glu Val Gln Val Gly Phe Gly Arg Val
1               5                   10                  15

Gly

<210> SEQ ID NO 18
<211> LENGTH: 17
<212> TYPE: PRT
<213> ORGANISM: Bos taurus

<400> SEQUENCE: 18

Gly Gly Val Phe Ile Ala Asp Glu Val Gln Val Gly Phe Gly Arg Val
1               5                   10                  15

Gly

<210> SEQ ID NO 19
<211> LENGTH: 17
<212> TYPE: PRT
<213> ORGANISM: Mus musculus

<400> SEQUENCE: 19

Gly Gly Leu Phe Val Ala Asp Glu Ile Gln Val Gly Phe Gly Arg Ile
1               5                   10                  15

Gly

<210> SEQ ID NO 20
<211> LENGTH: 17
<212> TYPE: PRT
<213> ORGANISM: Oikopleura dioica

<400> SEQUENCE: 20

Gly Val Leu Thr Ile Ala Asp Glu Val Gln Val Gly Phe Gly Arg Val
1               5                   10                  15

Gly

<210> SEQ ID NO 21
<211> LENGTH: 17
<212> TYPE: PRT
<213> ORGANISM: Arabidopsis thaliana

<400> SEQUENCE: 21

Gly Gly Val Cys Ile Ala Asp Glu Val Gln Thr Gly Phe Gly Arg Thr
1               5                   10                  15

Gly

<210> SEQ ID NO 22
<211> LENGTH: 17
<212> TYPE: PRT
<213> ORGANISM: Zea mays

<400> SEQUENCE: 22

Gly Gly Leu Cys Ile Ala Asp Glu Val Gln Ala Gly Phe Ala Arg Val
1               5                   10                  15

Gly
```

```
-continued

<210> SEQ ID NO 23
<211> LENGTH: 17
<212> TYPE: PRT
<213> ORGANISM: Capsicum annuum

<400> SEQUENCE: 23

Gly Gly Val Cys Ile Ala Asp Glu Val Gln Thr Gly Phe Gly Arg Thr
1               5                   10                  15

Gly
```